United States Patent [19]

Johnson et al.

[11] 4,292,994
[45] Oct. 6, 1981

[54] RAW MILK TRANSFER SYSTEMS

[76] Inventors: Julius T. Johnson, 348 - 20th St., S.E., Cedar Rapids, Iowa 52406; Robert R. Johnson, 416 Jacolyn Dr., N.W., Cedar Rapids, Iowa 52405

[21] Appl. No.: 124,597

[22] Filed: Feb. 25, 1980

[51] Int. Cl.³ .............................................. B67D 5/02
[52] U.S. Cl. .................................. 137/351; 137/384; 137/565; 137/624.18; 366/140; 417/12
[58] Field of Search ........... 137/351, 384, 565, 624.18; 366/140; 417/12

[56] References Cited

U.S. PATENT DOCUMENTS 2,623,449  12/1952  Losee .............................. 366/140 X

*Primary Examiner*—Gerald A. Michalsky
*Attorney, Agent, or Firm*—Matthew C. Thompson

[57] ABSTRACT

Electro-mechanical, milk transfer systems which interlock the dairy farmer's milk holding tank agitator and the pump for drawing milk from the tank into a milk transport vehicle to preclude energization of the pump until the agitator has operated for a minimum, predetermined time; tamper proof circumvention-preventing devices to preclude by-pass of the interlock systems during milk transfer to the transport vehicle; and milk sample-taking units for automatically taking one or more samples of the milk being pumped into the transport vehicle.

7 Claims, 8 Drawing Figures

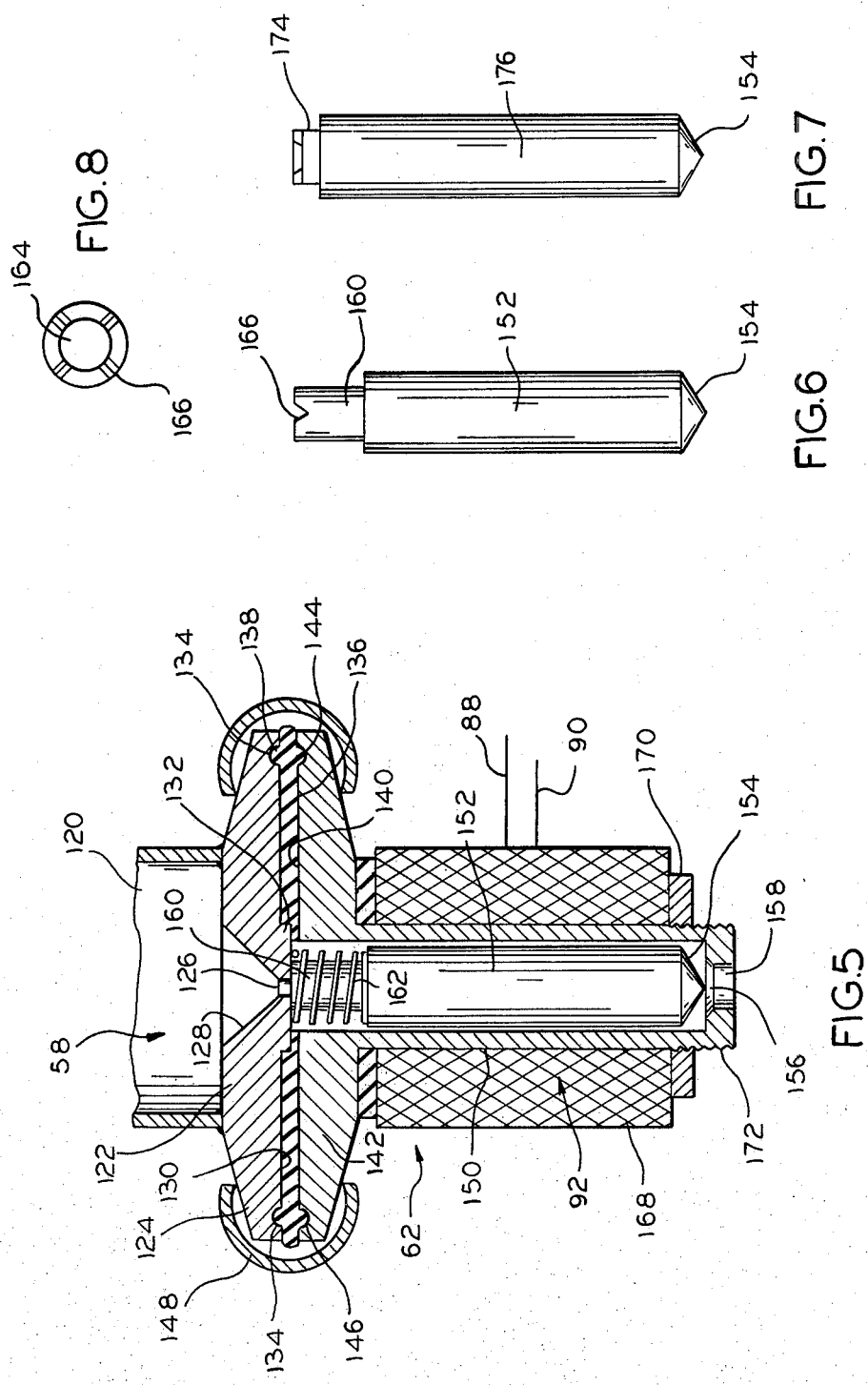

RAW MILK TRANSFER SYSTEMS

BACKGROUND

Raw milk is stored on dairy farms and combined dairy/agricultural farms and the like in milk holding tanks until the milk is collected and transported by truck to a dairy plant. Typically, and for the purposes of this invention, the milk holding tank has an agitator, e.g., an electric-motor-driven impeller, for agitating and making homogeneous the milk in the holding tank.

Raw milk purchase price, inter alia, depends on its total volume and on the butterfat content of the raw milk. As is well known, raw milk stratifies into an upper, cream layer which has a much higher butterfat content and lower proportionate volume than does the milk's lower layer. It is therefore important to both the dairy farmer seller and the dairy plant purchaser to ascertain at the time of collection of the raw milk both its total volume (e.g., by a flow meter or by measuring the depth of the raw milk in the holding tank before pumping is begun) and its average butterfat content.

Most, if not all, states have regulations calling for determination of average butterfat content of raw milk at the time of collection by requiring that the holding tank agitator be operated for a minimum, specified time, e.g., five to ten minutes, and then taking a sample of milk from the tank. Typically, the milk hauler takes such sample with a long handle dipper and pours it into a marked receptacle. The marked receptacle, and the total volume of raw milk collected from each tank, are given to the dairy plant for analysis of butterfat content per unit volume and calculation from volume and average butterfat content of the purchase price of the raw milk from each holding tank and/or seller. In a typical day, a milk hauler will make several collections from different sellers of raw milk before he returns to the dairy plant. The vehicle's tank contains a mixture of raw milk from the different farm sites.

The time of agitation of the raw milk is usually at the control and option of the milk hauler. If he is hurried or is careless, he may agitate for less than the minimum time specified in a state's regulations with the result that the raw milk has not been agitated enough to attain homogenity of the differing butterfat contents in cream and milk layers in the tank. If the hauler samples such inadequately agitated raw milk, his sample more than likely will not be representative of the true, average butterfat content of the raw milk in the tank. This works to the disadvantage of the seller or the purchaser—depending on whether the sample contained a disproportionately higher or disproportionately low butterfat content, vis a vis the true, average butterfat content.

THE INVENTION

This invention pertains to reasonably foolproof, tamper proof electro-mechanical systems which assure that the raw milk in the holding tank will be agitated for a minimum or specified, predetermined time before the milk hauler can begin to pump the tank contents into his transport vehicle. Special electro-mechanical controls in a sealed enclosure mounted on the vehicle preclude deliberate by-pass of the systems at the site of each collection of raw milk. Additionally, the systems incorporate in the lines of pumped, raw milk a sample-taking unit which is activated one or more times as the raw milk is being pumped from the holding tank to the milk transport vehicle. Such activation, most preferably, involves an electrically-operated valve in the sample-taking unit which is electrically coupled to and energized by an electric timer unit in the sealed enclosure, or by a stepping relay.

The pump is also electrically coupled to the stepping relay or to an electric timer unit. The latter unit, and preferably both timer units if two are used, is/are energized by a circuit having an electric cord or cable with special plug whose specially oriented prongs or blades fit only into an electrically active, special socket mounted on or near each raw milk holding tank. The timer unit(s) or stepping relay is/are mounted in a tamper proof, sealed enclosure mounted on the transport vehicle. The cord or cable extends from the enclosure at a length which will allow its special plug to reach the special socket at each site.

The contacts of the special plug and special socket preferably have a unique, or at least uncommon, shape and/or arrangement to assure that the timer unit or stepping relay which energizes the vehicle's pump cannot be connected to a socket in any electric circuit except that of the special socket. This socket has two contacts wired to the power wires for the electric motor of the tank agitator. When the switch to energize this motor is closed, the two socket contacts become live. This starts the electric timer unit or relay, which controls the circuit for the vehicle's pump. Such circuit remains open for a predetermined time, as set on the timer unit or by the number of steps on the relay, e.g., five or ten minutes as specified by a state's regulations. During this time, the tank agitator continues to run, as does the timer unit or relay. At the end of the pre-set time, the timer unit or relay closes the pump's circuit, and it begins to draw raw milk from the tank into the vehicle.

The timer unit or stepping relay closes the circuit of a solenoid switch connected through the circuit of the timer unit or to a plurality of sequential step contacts on the stepping relay. The pump, energized by the power from the special socket/plug connection, continues to run until the agitator is deenergized or the plug is disconnected. It is normally preferred to keep the tank agitator running until the tank is empty.

Should it be preferred to allow the pump to run, after expiration of the preset time of agitation before the pump is activated, without the necessity of continuing the agitation until the tank is empty, the special plug and socket may have two additional contacts which also provide line power through the cable to the solenoid switch through two additional wires. These wires, however, must be connected through the timer unit so that their circuit is closed only after the timer has run for its pre-set time. With such additional circuitry, the pump will continue to run even after the agitator switch has been opened.

In the alternative, such additional wires could be connected through another electrical timer unit, the unit for the sample-taking device, in a manner wherein the circuit for these additional wires is closed only after the sampling operation has been completed. This assures that the pump cannot be energized by the alternative circuit to its solenoid switch until completion of the sampling—thereby assuring that the tank's agitator will maintain homogeneity of the raw milk through the sample taking time(s).

The additional timer unit may be energized simultaneously with the first-mentioned timer unit from the circuit of the first mentioned pair of plug/socket contacts and wires, or it may begin to run through appropriate contacts in the first-mentioned timer unit or in the stepping relay, which contacts close the circuit of the second timer when the first timer has run its pre-set time or after the stepping relay has stepped through a plurality of its contacts over said pre-set time. In either case, the additional timer unit preferably energizes an electrically-operated valve in the sample-taking unit at least twice. The first occasion, generally about 30-60 seconds after the pump begins to run, opens the sample-taking units solenoid valve to flush out residual raw milk from an earlier seller, or washing liquid, in the sampling unit. This sample is discarded. The second occasion, at any time thereafter, opens the valve again in a sampling pulse of 5-30 seconds duration. The milk hauler collects the sample in a pre-marked container to give to the dairy plant for butterfat analysis.

One sampling usually is enough as long as the raw milk in the tank has had the regulation-required time of agitating, which should continue at least through the sampling step. However, multiple samplings may be made, if desired, as the emptying of the tank progresses by simply using a timer unit which pulses the solenoid valve at several predetermined intervals, e.g., every 2-5 minutes.

The sample-taking unit is of relatively simple construction. It comprises a T-coupling placed in a preferably horizontal leg of the milk flow conduit system on the back or side of the transportation vehicle. The third leg of the T-coupling has a circularly flanged downstream end, which is closed off by a disc having a small, axial passage for flow of milk sample. The flanged end is coupled by a quick-disconnect ring clamp to a correspondingly shaped circular flange of a disc on the upstream end of a sample discharge tube.

The latter has at its downstream end a ported valve seat. A cylindrical valve body made of or containing a core of magnetized metal is loosely slidable in the tube, its lower end being shaped to seat tightly on the valve seat. A solenoid surrounds the tube. When energized, it draws the valve body off the valve seat. Sampled milk flows through the small axial passage into the tube, where it flows in the annular space between the tube and the loose-fitted cylindrical valve body and out of the discharge port.

When the solenoid is not energized, pressure of the pumped milk against the upstream surfaces of the valve body and an upstream valve stem thereon keeps the valve tightly seated on the valve seat. The valve optionally may have a coil spring about its stem to yieldingly press the valve body against the valve seat. If the tube hangs vertically downward, gravity will also assist in keeping the valve body seated on the valve seat.

PREFERRED EMBODIMENTS

Preferred forms of the invention and preferred modes of using same are illustrated in the drawings, wherein:

FIG. 4 is a plan view of a similar special electrical socket used at the sites of raw milk holding tanks on dairy farms and the like;

FIG. 5 is a diametric section of a milk sample-taking unit;

FIGS. 6 and 7 are respective side elevations, partly in section (FIG. 7), of two embodiments of valve bodies for the sampling unit of FIG. 5: and FIG. 8 is a top plan view of both of said bodies.

Figure 1:
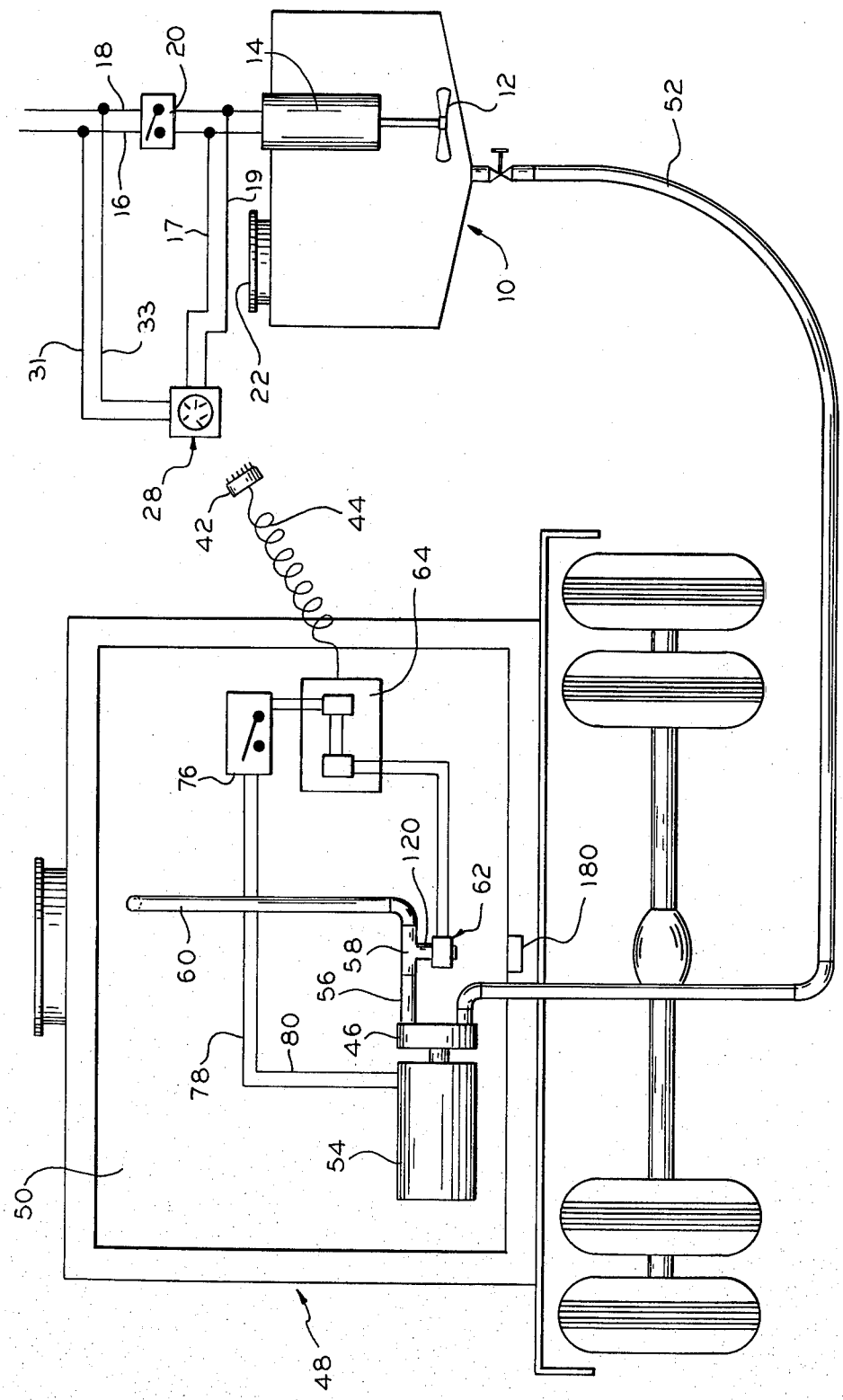
FIG. 1 is a schematic view of the raw milk transfer system including a raw milk holding tank with an electrically-powered agitator, the rear of a milk transport vehicle, the milk transfer hose connecting the tank with the pump and the piping on the rear of the vehicle, and the electro-mechanical components of the system with schematic wiring.

Referring to the drawings, the raw milk holding tank 10 has a rotary impeller agitator 12 driven by an electric motor 14. Two a/c power wires 16,18 connect the motor with an a/c power source, e.g., a 110-120 volt line through the manual switch 20. The tank has a covered manhole 22 for entering the tank for cleaning, repairs or maintenance, taking manual samples, e.g., with a dipper, measuring the depth of liquid, etc.

Two circuit wires 17,19 connect the wires 16,18 to an electrical socket or receptable 28 mounted on or near the tank 10. The socket (see FIG. 4) has four live contacts 30,32,34,36, and two blade receiving openings 38,40. As can be seen from FIG. 4, the contacts and openings have a unique or unusual orientation relative to each other. The blades of the plug 42 which enter these contacts have a like orientation—thereby assuring that plug 42 cannot be plugged into another, ordinary a/c wired socket in order to bypass the electro-mechanical system's interlock of the power circuit of electric motor 14 and the circuit for energizing the motor of the milk pump on the transport vehicle.

Wires 17,19, for example, may be coupled to contacts 34,36. The system may include optionally wires 31,33 providing a direct connection between the a/c power source and contacts 30,32. The connection of wires 31,33 and their contacts 30,32 to the a/c power source, e.g., wires 16,18, is preferred because they are used in an emergency power bypass to keep the pump running in the event of malfunction in the timer(s) or stepping relay circuits, as hereinafter described, before the tank is emptied.

The stretchable, coil wound, electric cable 44 contains at least the wires 24,26 and preferably, though optionally, contains the wires 25,27. These wires are connected to the four blades of the plug 42 corresponding to socket contacts 30,32,34 and 36.

The cable 44 provides the power to drive the motor 54 of the milk pump 46, which is mounted on the milk transportation vehicle 48. This vehicle, e.g., a milk tank truck with a large milk-receiving tank 50, is parked next to the tank 10. A milk transfer hose 52 is coupled to the tank 10 and the pump 46. Milk is drawn by the pump through the hose and then pumped under pressure through the horizontal leg 56, the T-connection 58, and the vertical leg 60 of the vehicle's piping into the tank 50. The T-connection is used to mount the sampling-taking unit 62, hereinafter described in detail, in the vehicle's piping system.

Figure 2:
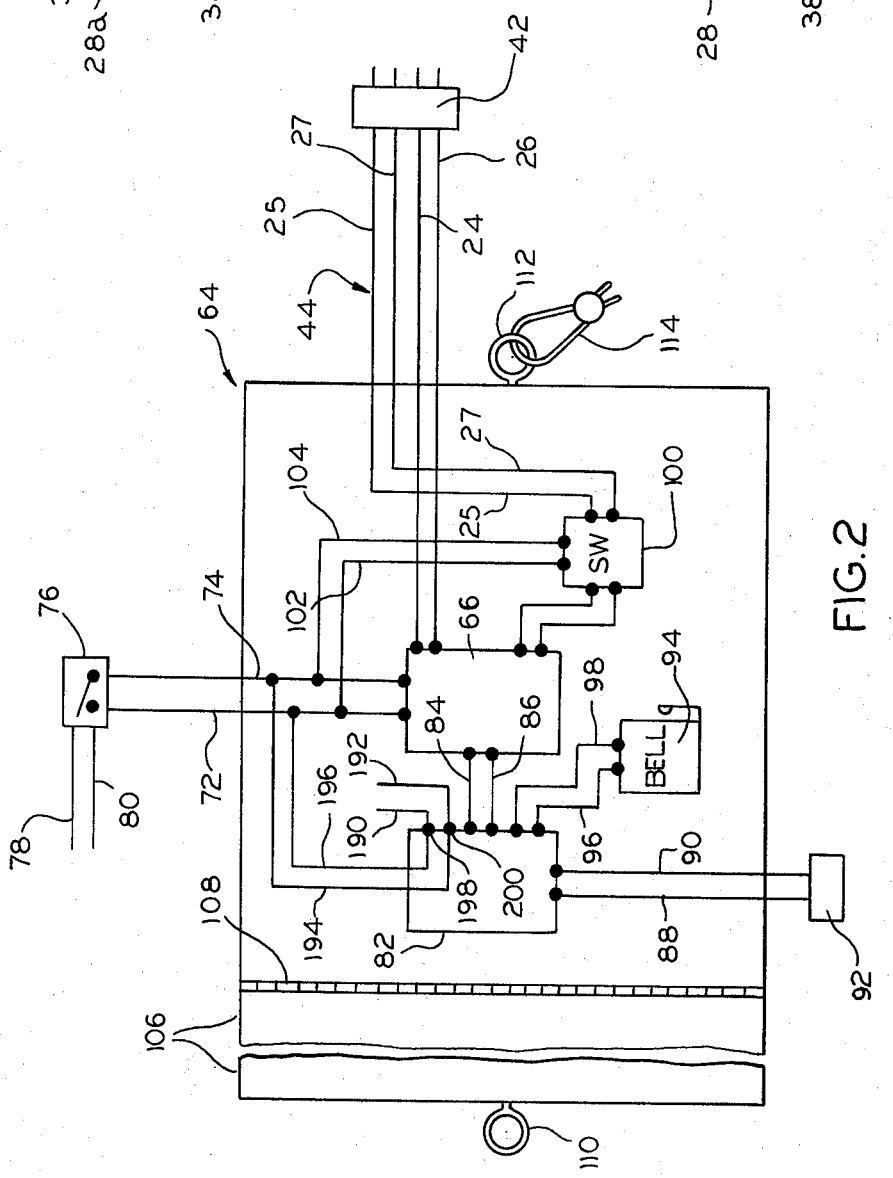
FIG. 2 is a schematic view of a sealable, tamper proof enclosure for certain components of the electromechanical system.

The electro-mechanical components of the system are partly or wholly mounted in a tamper proof enclosure or box 64, which in turn is mounted on the vehicle 48. Referring especially to FIG. 2, the enclosure 64 houses an electric timer unit 66 of known construction, e.g., Eagle Signal Miniflex timer BG 1096. The wires 24,26 are wired to the two blades of the plug 42 for socket contacts 34,36 and to the timer unit 66. Therefore, timer unit 66 is not energized until the switch 20 in the agitator's motor circuit is closed. The timer unit then begins to run (and continues to run) only while the raw milk is being agitated. It runs for its programmed time, e.g., five or ten minutes. At the end of this period, the timer unit closes contacts which connect the wires 72,74 with wires 24,26. Wires 72,74 are connected through the solenoid switch 76, which closes when energized through the wires 72,74. The contacts of the solenoid switch 76 connect wires 72,74 with wires 78,80—thereby energizing the motor 54 of the pump 48. The pump begins and continues to run as long as the plug 42 remains in the socket 28 and the switch 20 remains closed. The tank begins to empty with its raw milk still under agitation.

The enclosure 64 contains an additional, second timer unit 82 which controls the liquid sampling operation. Wires 84,86 connect timer unit 66 with timer unit 82. They may be wired so that timer unit 82 begins to run at the same time as does timer unit 66, e.g., by a direct connection to wires 24,26, or so that the timer unit 82 begins to run only when timer unit 66 reaches the end of its pre-set program time (the aforesaid five or ten minutes), e.g., by direct connection to wires 72,74.

Wires 88,90 connect contacts of the timer unit 82 with the solenoid 92 of the sample taking unit 62. In the manner later described, the contacts close at least twice after the pump has begun to run, thereby discharging through the sampling unit a first volume of raw milk which flushes out residual raw milk (or washing liquid) in the sampling unit and which is discarded, and later at least a second volume of raw milk which is collected as the representative sample (or a part of a plurality of sampled volumes).

The timer unit 82 may be connected to a buzzer or bell 94 by wires 96,98 connected to contacts of the timer unit 82 so that the buzzer or bell sounds when the first, flushing volume of raw milk has been discharged and thereby warns the milk hauler to prepare to collect the next sample volume(s) to be collected in a marked container.

The enclosure 64 may also contain a manual emergency override switch 100 connected by the wires 25,27 to the blades of the plug 42 for the hot wired contacts 30,32. When switch 100 is closed, a direct connection between the cable wires 25,27 and the solenoid switch's wires 72,74 is provided through wires 102,104. In case of malfunction of time unit 66, the enclosure may be opened by breaking its wire or tape, certifying seal 114 to gain access to the override switch 100 in the enclosure.

The enclosure 64 is an ordinary, weather tight, metal box having a door 106 (shown in fragment) hingedly mounted by a non-removable hinge 108 and preferably having a key lock to keep it closed. The box and the door each have juxtaposed metal rings 110,112 through which the wire or metal tape of a certified, sealed loop 114 are run. Should the enclosure be opened, as in case of emergency, the seal would be broken—warning the dairy plant that at least some of the raw milk being delivered may not have been sampled and/or collected under the program control of the electro-mechanical system.

Referring now particularly to FIGS. 5–8, the third leg 120 of the T-connection 58 has a circular disc 122 across its downstream end. The disc 122 has a tapered, ring flange 124 and a small, axial orifice 126 downstream from the tapered, concentric passage 128 in the center of the disc. The disc's downstream face 130 has a small, concentric ring 132 about the orifice 126. This face also has a concentric, circular groove 134 in the flange area. The circular rib 138 of the elastomer gasket washer 136 seats in the groove. The upstream, opposing face 140 of the tapered flange disc 142 on the upstream end of the sample discharge tube 150 has a concentric, circular groove 144 in which is seated the circular rib 146 on the opposite side of the gasket washer 136. The two flanged discs 122 and 142 are releasably pressed together with the gasket washer therebetween by the quick release ring clamp 148, a well known type of quick release clamp being shown in J. T. Johnson U.S. Pat. No. 3,229,527. The ring 132 presses tightly against the inner portion of the gasket washer 136 about its center hole—giving an annular fluid tight seal about the orifice 126.

The simple discharge tube 150 contains a cylindrical, loose fitting valve body 152 having a conically tapered downstream end 154 which seats tightly on the correspondingly tapered valve seat 156 about the tube's discharge port 158. The valve body has a concentric, upstream valve stem 160. A coil spring 162 is compressed between the valve body 152 and the ring 132 and resiliently biases the valve body against the valve seat 156.

The upstream face of the valve stem 160, when the valve body is in open position, bears against the ring 132. To keep it from sealing off the orifice 126, the upstream face has an axially central cavity 164 intersected by radial notches 166. This allows the milk to flow through the orifice into the cavity, through the notches, about the valve stem 160, through the small annular clearance between the valve body 152 and tube 150 and out of the discharge port 158.

The valve body 152 is made of magnetic or magnetizable metal (or a body with a ferro-magnetic metal core sheathed in a magnetically conductible metal or plastic is so made) having a polarity in the magnetic field created by the winding of the solenoid 168 to move the valve body upstream in the tube 150 to unseat the valve. The valve remains open as long as the solenoid is energized. When deenergized, the spring 162, gravity if the tube 150 hangs downwardly as illustrated, and the milk's pressure on the transverse, upstream surfaces of the valve stem and valve body press the valve body to the closed, seated position.

The solenoid 168 is mounted about the tube 150 by a nut 170 threaded on the threads 172 at the downstream end of the tube. The valve stem 174 on the valve body 176 (FIG. 7) is shorter (and the valve body is correspondingly longer) than in the case of the spring-loaded valve of FIGS. 5 and 6. This valve, without spring bias, is urged toward valve seating position by gravity and the line pressure of the pumped raw milk.

Figure 3:
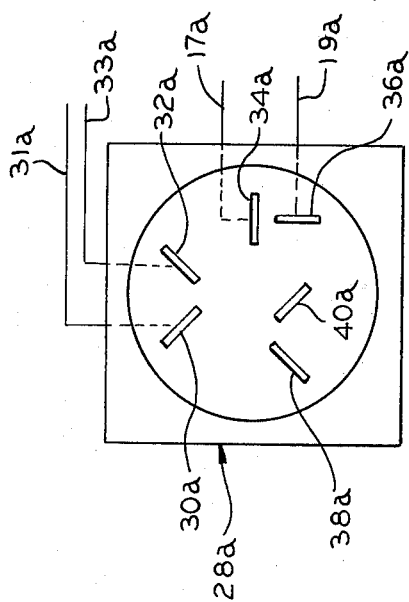
FIG. 3 is a plan view of a special electrical socket used to energize the vehicle's pump while its tank is flushed in the dairy plant with cleaning liquid.

The socket 28a shown in FIG. 3 is designed for use in the dairy plant. Its contacts have the same orientation as those in the farm socket shown in FIG. 4, whereby the blades of the plug 42 can be inserted. Contacts 34a,36a are live and engage the plug's blades which are connected by the wires 24,26 to the timer unit 66. This allows the milk hauler to run the pump 46, after the timer has run its pre-set time, to circulate cleaning liquid through the pump, the piping, the hose and the tank of the vehicle. The sampling unit, after its timer unit 82 reaches the pre-set solenoid valve energizing period, would be flushed with the circulating cleaning liquid in the sample withdrawal periods.

Returning briefly to FIG. 2, though preferably active wires, the cable's second pair of wires 25,27 may be omitted entirely or (b) they may or may not be live wires, depending on a particular farm's wiring of its socket 28, notably the contacts 30,32. If these contacts are connected to the power wires 31,33, the cable's wires 25,27 may be used to keep the vehicle's pump energized in an emergency situation. For example, should the timer unit 66 or its wiring malfunction so that solenoid switch 76 for the pump's circuit either does not close at all or opens as the tank 10 is being emptied, causing the pump motor 54 to stop, the milk hauler breaks the seal 114 on the enclosure 64, opens the latter, and closes emergency, manual switch 100 inside the enclosure. This closes solenoid switch 76 and reenergizes the pump motor 54 so that the milk holding tank 10 can be emptied.

Figure 4:
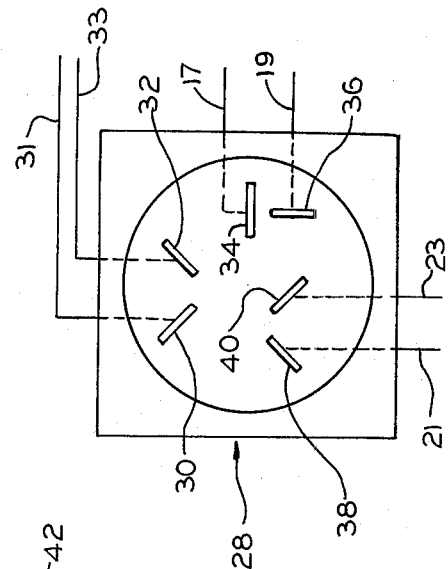

Referring to FIG. 3, the socket 28a in the dairy plant has contact pairs 30a, 32a and 34a,36a corresponding in position and orientation to the farm sockets' contact pairs 30,32 and 34,36 (FIG. 4). The socket 28a also has a pair of openings 38a, 40a corresponding in position and orientation to the farm sockets' openings 38,40, whereby the six blades of plug 42 may be inserted into the dairy plant socket 28a, as well as into farm socket 28.

Contacts 30a,32a and contacts 34a,36a are wired by wires directly to an a/c power source. When plug 42 is inserted in socket 28a, after the contents of vehicle tank 50 have been emptied into the dairy plant's tanks, the timer unit 66 begins to run by power supplied via contacts 34a,36a and cable wires 25,27. As the timer unit runs its pre-set five or ten minutes prior to closing solenoid switch 76 and its circuit to pump motor 54, the tank 50 is rinsed and partially filled with a cleansing, sanitizing liquid. The hose 52 is coupled to a drain outlet 180 (FIG. 1) in the bottom of vehicle tank 50. When the timer unit 66 closes the solenoid switch 76, the pump 46 begins to circulate the cleansing, sanitizing liquid in tank 50 through drain 180, hose 52, pump 46, piping leg 56, T-coupling 58 and piping leg 60 back into the tank. The pump 46 is run until the valve of the sample-taking unit 62 has been opened at least once by current in the wires 88,90 from the second timer unit 82. This flushes, cleanses and sanitizes the sample taking unit 62. Thereafter, the plug 42 may be disconnected from the socket 28a, after which the tank 50 is drained.

As an alternative to using two timers, the control of the solenoid switch for the circuit of the pump's electric motor, the solenoid valve on the sample-taking unit and the warning buzzer may be accomplished with a single stepping relay which is moved step-by-step from contact to contact by a step pulser, e.g., a timer which gives timed, spaced electrical pulses. Each pulse moves the stepping relay one step. To illustrate, let it be assumed that the minimum agitation time required by a state's laws and regulations is five minutes. The periods for opening the valve of the sample-taking unit 62 is 0.5 to 3 seconds for the flushing and 0.5 to 3 seconds for a single taking of the sample to be collected by the milk hauler.

Referring to the chart below, the solid vertical lines under Agitator Motor, Solenoid Switch, Solenoid Valve and Warning Buzzer designate when their respective circuits are active (closed) and the wires (numbers in parenthesis) used to supply the electric power. The agitator's motor is energized by wires 16,18 from time zero through at least 420 seconds (7 minutes). Every 30 seconds, the step pulser, energized through wires 24,26, issues a short pulse (the short vertical lines under Step Pulser) which causes the stepping relay to move sequentially through steps 1-15. The relay contacts for steps 1 through 11 are unwired. At step 12 through 15, after expiration of five minutes of stepping operation of the stepping relay, the relay's contacts are wired to the solenoid switch 76. The pump's motor 54 is energized and begins to run through steps 12, 13, 14 and 15. Simultaneously at step 12, the solenoid 168 of the sample-taking unit 62 is energized for 0.5 to 3 seconds. The relays contacts at steps 12,13 and 14 are wired to the timer unit 82 (FIG. 2). The stepping relay replaces timer unit 66. As timer unit 82 begins to run, it gives a short pulse of 0.5–3 seconds through wires 88,90 to the solenoid 168 of the sample-taking unit. This flushes the sample-taking unit for 0.5–3 seconds. The timer unit 82 next pulses the buzzer or bell 94 through wires 96,98 for 30 seconds during the relay's dwell at step 13—warning the milk hauler that a sample discharge is imminent. During the relay's dwell at step 14, the timer unit 82 again pulses the solenoid 168 of the sample-taking unit via wires 88,90 for 0.5–3 seconds. The milk hauler collects and marks this sample.

The relay may stop at step 15. Its contacts at step 15 are connected to wires 72,74 or directly to solenoid switch 76 to keep the pump motor 54 energized until the farm tank 10 is empty. When plug 42 is disconnected, the stepping relay returns automatically to zero or home position.

CHART

| Sec. | Min. | Agitator Motor | Step Pulser | Step | Solenoid Switch | Solenoid Valve | Warning Buzzer |
|---|---|---|---|---|---|---|---|
| 0 | 0 | | ' | 1 | | | |
| 30 | | | ' | 2 | | | |
| 60 | 1 | | ' | 3 | | | |
| 90 | | | ' | 4 | | | |
| 120 | 2 | (16,18) | ' | 5 | | | |
| 150 | | | ' (24,26) | 6 | | | |
| 180 | 3 | | ' | 7 | | | |
| 210 | | | ' | 8 | | | |
| 240 | 4 | | ' | 9 | | | |
| 270 | | | ' | 10 | | | |
| 300 | 5 | | ' | 11 | | | |

CHART-continued

| Sec. | Min. | Agitator Motor | Step Pulser | Step | Solenoid Switch | Solenoid Valve | Warning Buzzer |
|---|---|---|---|---|---|---|---|
| 330 |   |   | ' | 12 |   |   | Flush(88,90) |
| 360 | 6 |   | ' | 13 |   |   | (96,98) |
| 390 |   |   | ' | 14 |   |   | Sample(88,90) |
| 420 | 7 |   | ' | 15 |   |   |   |
| etc. |   |   |   |   | (24,26) |   |   |
|   |   |   |   |   | (72,74) |   |   |

Continuous agitation of the raw milk in the farm tank 10 during the entire time the tank is being emptied has the advantage of reducing the amount of cream which sticks to the walls of the tank 10. However, the farm tank's socket 28, the blades of plug 42, and the wiring in the cable 44 may be modified to allow the agitator 12 to be stopped after the samples or last of several samples are collected.

In the earlier described embodiments, the openings or contacts 38,40 of the farm socket 28 (FIG. 4) are dummy openings or dummy (unwired) contacts for the plug's corresponding blades. Alternatively, the contacts 38,40 can be wired to serve, respectively, as ground connections for the two circuits connected to socket contact pairs 30,32 and 34,36.

In areas where accepted procedures or laws and/or regulations dictate that the agitator 12 must be or preferably is stopped before the farm tank 10 is completely emptied, the contacts 38,40 can serve another function. Here the contacts are hot wired by wires 21,23 to an a/c source. The cable 44 contains two additional wires 190,192 (shown inside enclosure 64 but not in the cable 44) which wires are connected at one end to the plug's blades for contacts 38,40 and at the other end to one side of open-close contacts 198,200 on timer unit 82, e.g., Eagle Signal Company's Miniflex timer DA 1212 A6 or DG 102 A 605. Wires 194,196 connect the other side of the open-close contacts 198,200 with the wires 72,74.

Contacts 198,200 are closed only after the timer unit 82 has pulsed via wires 88,90 the sample-taking unit's solenoid 92 to take the only sample (or the last of several samples). The contacts 198,200 remain closed until the plug 42 is disconnected. This provides a parallel, bypass circuit to solenoid switch 76—which keeps the pump motor 54 running even if the switch 20 for the agitator motor circuit 16,18 is opened to stop the agitation. In such case, the circuit via wires 24,26; timer unit 66; the wires 72,74 is broken by the opening of the circuit to the farm socket contacts 34,36 via wires 17,19. The bypass circuit via wires 21,23; contacts 38,40 and the inserted plug blades; wires 190,192; timer unit 82 and its contacts 198,200; wires 194,196; and wires 72,74 takes over to keep solenoid switch 76 energized and closed and the pump motor 54 energized and running. At the same time, the circuitry and electrical components assure that the bypass circuit cannot take over until the sample or last of several samples has been taken—assuring that the farm tank's agitator will be run at least through the sample-taking-time(s).

The openings 38a, 40a (without or without contacts therebehind) in the dairy plant socket 28a (FIG. 3) may be dummy openings or dummy contacts (unwired), or their contacts may be wired as respective grounds for the wire pairs 31a,33a and 17a,19a.

The milk transfer systems herein described offer many new and important advantages over existing methods and equipment heretofore used to transfer and sample raw milk at the farm. The systems ensure that the letter and intent of the law is followed by preventing the farmer's raw milk from being transferred to a tanker vehicle until the milk has been agitated in the holding tank for the full period required by the laws and regulations of the jurisdiction. The milk sampling features of these systems insure an accurate, truly representative sample of the entire volume in the tank by automatically collecting the sample(s) from thoroughly and continuously agitated raw milk as it is pumped from the holding tank into the transport vehicle.

We claim:

1. A system for transferring milk from a holding tank having an electric motor driven agitator to the tank of a milk transport vehicle which comprises milk transfer conduit means for conveying milk from the holding tank to the vehicle's tank, a pump driven by an electric motor for pumping milk through said conduit means, an electrical circuit including power wires for energizing the electric motor of said agitator through an on-off switch, an electrical socket having a first set of socket contacts wired to said power wires whereby said first set of contacts are energized when said on-off switch is closed and are deenergized when said switch is open, an electrical connector having a first set of connector contacts removably engageable with said first set of socket contacts, an electrical component enclosure, an electrical timer in said enclosure, an electric cable with wires connecting said first set of connector contacts with said timer whereby said timer is energized when said agitator's electric motor is energized, and wires connecting said pump's electric motor to a power source through open-close contacts closeable by said timer after it has run a predetermined time whereby said pump's electric motor is idle during the initial agitation of said milk in said holding tank while the timer runs its predetermined time and becomes energized at the expiration of said predetermined time by the closing of said open-close contacts by said timer to pump the milk from said holding tank to the vehicle tank.

2. A system as claimed in claim 1, wherein said milk transfer conduit means includes milk sample-taking means having an electrically energized valve, a second timer mounted in said enclosure, circuit means to run said second timer for a period after the expiration of the predetermined time for said first timer, means on said second timer to energize said electrically operated valve for at least two short periods of time to open said valve a first short period to flush said sample-taking unit of residual liquid therein and thereafter for at least a short second period to withdraw at least one small milk sample from the milk being pumped through said conduit means after the expiration of said predetermined time.

3. A system as claimed in claim 2, wherein said enclosure is substantially tamper-proof and has a door which in closed position is sealed by a certified seal member, whereby said timers and the wiring therewith within said enclosure are not accessible without first breaking said seal member.

4. A system as claimed in claim 1, whereby said enclosure is substantially tamper-proof and has a door which in closed position is sealed by a certified seal member, whereby said timer and the wiring therewith within said enclosure are not accessible without first breaking said seal member.

5. A system as claimed in claim 1, whereby said enclosure is substantially tamper-proof and has a door which in closed position is sealed by a certified seal member, whereby said timer and the wiring therewith within said enclosure are not accessible without first breaking said seal member, and a manually closable, override switch mounted in said enclosure and wired to an electric plug connectable to an electric power source and wired to the open-close contacts for the circuit of said pump's electric motor to permit emergency operation of said pump without involvement by the timer.

6. A system as claimed in claim 1, wherein said milk transfer conduit means includes a T-coupling therein, a milk sample withdrawal tube coupled to the third leg of said T-coupling, a valve body loosely and slidably mounted in said tube, a sample discharge port at the downstream end of said tube, a valve seat about said port, a matingly shaped end of said valve body resting sealingly against said seat to normally close said port, and means to move said valve body away from said seat and thereby open said port to flow of milk samples therethrough.

7. A system as claimed in claim 6, wherein said means is a solenoid winding about said tube, and said valve body comprises at least in part a magnetizable or magnetized ferro-magnetic metal having a polarity which moves said valve body away from said seat when said solenoid is energized.

* * * * *